(12) United States Patent
Gerber et al.

(10) Patent No.: US 7,067,299 B2
(45) Date of Patent: Jun. 27, 2006

(54) **MATERIALS AND METHODS FOR *IN VITRO* PRODUCTION OF BACTERIA**

(75) Inventors: John F. Gerber, Gainesville, FL (US); Thomas E. Hewlett, Gainesville, FL (US); Kelly S. Smith, Gainesville, FL (US); James H. White, Gainesville, FL (US)

(73) Assignees: Pasteuria Bioscience, LLC, Alachua, FL (US); CDG Laboratories, Inc., Gainesville, FL (US)

( * ) Notice: Subject to any disclaimer, the term of this patent is extended or adjusted under 35 U.S.C. 154(b) by 165 days.

(21) Appl. No.: 10/460,581

(22) Filed: Jun. 11, 2003

(65) Prior Publication Data
US 2003/0232422 A1    Dec. 18, 2003

Related U.S. Application Data

(60) Provisional application No. 60/388,008, filed on Jun. 11, 2002.

(51) Int. Cl.
*C12N 1/20* (2006.01)
*C12N 1/00* (2006.01)

(52) U.S. Cl. .................. 435/252.2; 435/243; 435/253.6
(58) Field of Classification Search ............ 435/252.1, 435/252.2, 243, 253.6
See application file for complete search history.

(56) References Cited

U.S. PATENT DOCUMENTS 3,071,519 A * 1/1963 Bonnefoi ................... 435/242

4,824,671 A * 4/1989 Ellis et al. ............. 424/195.16
5,094,954 A    3/1992 Previc et al.
5,378,460 A * 1/1995 Zuckerman et al. ... 424/93.461

FOREIGN PATENT DOCUMENTS

| JP | 06165670 A | 6/1994 |
|---|---|---|
| WO | WO 99/05325 | 2/1999 |
| WO | WO 01/11017 A2 | 2/2001 |

OTHER PUBLICATIONS

Hewlett, Thomas E., John F. Gerber, Kelly S. Smith, James H. White (2002) "*In Vitro Culture of Pasteuria penetrans*" *Nematology* 4(2):152-153.
ATCC: *Bacteria & Bacteriophages*, (1992), pp. 478-479, 18th Ed., Published by American Type Culture Collection: Rockville, Maryland.
Bishop, A.H. and D.J. Ellar, "Attempts to Culture *Pasteuria penetrans in vitro,*" *Biocontrol Science and Technology*, (1991), vol. 1, pp. 101-114.

(Continued)

*Primary Examiner*—Vera Afremova
(74) *Attorney, Agent, or Firm*—Saliwanchik, Lloyd & Saliwanchik

(57) ABSTRACT

The subject invention provides novel and advantageous methods for growing bacteria. The methods of the subject invention are particularly advantageous for growing parasitic bacteria in vitro, without the presence of host tissue. In one embodiment of the subject invention, *Pasteuria* endospores, such as those that infect the rootknot nematode *Meloidogyne arenaria* or other host nematodes, are grown in vitro under acidic conditions. The process of the subject invention is highly advantageous because *Pasteuria* can be grown in the absence of nematode tissue.

12 Claims, 5 Drawing Sheets

OTHER PUBLICATIONS

Brock, T. et al. *Biology of Microorganisms*, (1991), Simon &Schuster, Englewood, Cliffs, NJ; 6th Ed. pp. 474-483.

Chen and Dickson, "Review of *Pasteuria penetrans*: Biology, ecology, and biological control potential." *J. Nematology* (1998), vol. 30, No. 3, pp. 313-340.

Duponnois, R. et al. "Beneficial effects of *Enterobacter cloacae* and *Pseudomonas mendocina* for biocontrol of *Meloidogyne incognita* with the endospore-forming bacterium *Pasteuria penetrans*." *Nematology*, (1999), vol. 1, No. 1, pp. 95-101.

Duponnois, R. and A.M. BA. "Influence of the Microbial Community of a Sahel Soil on the Interactions Between *Meloidogyne Javanica* and *Pasteuria penetrans*." *Int. J. Nematol. Res.* (1998), vol. 44, pp. 331-344.

Fire, A. et al. "Potent and specific genetic interference by double-stranded RNA in *Caenorhabditis elegans*." *Nature* (1998), vol. 391, pp. 806-811.

Reise, R.W. et al. *Abstracts of the 27th Annual Meeting Society of Nematologists* (1988), p. 75, abstract.

Reise, R.W. et al. "Limited In-vitro Cultivation of *Pasteuria-nishizawe*." *Journal of Nematology* (1991), vol. 23, No. 4, pp. 547-548, abstract.

Verdeho, S. and R. Mankau. "Culture of *Pasteuria penetrans* in *Meloidogyne incognita* on oligoxenic excised tomato root culture," *Journal of Nematology* (1986), vol. 18, p. 635, abstract.

Dabire, K.R. et al. "Indirect effects of the bacterial soil aggregation on the distribution of *Pasteuria penetrans*, an obligate bacterial parasite of plant-parasitic nematodes," *Geodema* (2001), vol. 102, pp. 139-152.

Duponnois, R. et al. "Effect of the rhizosphere microflora on *Pasteuria penetrans* Parasitizing *Meloidogyne graminocola*," *Nematol. Medit*. (1997), vol. 25, pp. 99-103.

* cited by examiner

MATERIALS AND METHODS FOR IN VITRO PRODUCTION OF BACTERIA

CROSS-REFERENCE TO A RELATED APPLICATION

This application claims the benefit of provisional patent application Ser. No. 60/388,008, filed Jun. 11, 2002, which is hereby incorporated by reference in its entirety.

BACKGROUND OF INVENTION

This invention relates to methods for the production of *Pasteuria*, or *Pasteuria*-like, bacteria. These bacteria are able to produce endospores that have the unique and useful property of being able to attach to, infect, grow in, resporulate in, and kill certain types of phytopathogenic nematodes and other soil-dwelling nematodes. These phytopathogenic nematodes come from the phylum Nematoda, within the orders Tylenchida and Dorylamida.

Plant parasitic nematodes inflict crop losses to world agriculture currently estimated to total US $80 billion. Preventing this damage represents a significant challenge. With the impending loss of the fumigant methyl bromide in 2005, there is insufficient time to develop and register new synthetic compounds for nematode control.

Phytopathogenic nematodes are particularly difficult to control because they are covered with a thick, impermeable cuticle, or outer covering, and have very few sensory neurons. Since many pest control compounds operate as neurotoxins, the low number of neurons exposed by phytopathogenic nematodes decreases the effective target area for nematicidal compounds and has resulted in the development of nematicidal compounds with exquisitely high neurotoxic properties. Furthermore, because the phytopathogenic nematodes are found in soil or plant roots, exposing the phytopathogenic nematodes to control agents also is difficult to achieve and puts the water table at risk of contamination from those toxic compounds. The use of nematicides based on neurotoxins has been demonstrated to contaminate both ground and surface water. Consequently, many of these compounds are being removed from the market for public health reasons.

Fumigation of soil prior to planting is a popular method for controlling nematodes. One of the most popular fumigants, methyl bromide, is slated for removal from use because of its ozone destroying properties. However, this practice of soil fumigation kills organisms in soil indiscriminately and runs the risk of eliminating beneficial microbes as well as disease organisms. The overall market for an effective nematicide with benign environmental effects is estimated to approach one billion dollars on a world-wide basis.

The genus *Pasteuria* has several members that parasitize plant-parasitic nematodes, and it has been recognized as a potential biological control agent. Although bacteria of the *Pasteuria* group have a recognized potential for use as biorational control agents against phytopathogenic nematodes, their widespread use in commercial agriculture will depend on the availability of reliable methods for the large-scale production of bacteria having specificity against the phytopathogenic nematodes of concern to farmers.

*Pasteuria* was first described in 1888 by Metchnikoff (Annales de l'Institut Pasteur 2:165–170) as a parasite of water fleas. Subsequently, Cobb described a *Pasteuria* infection of the nematode *Dorylaimus bulbiferous* ($2^{nd}$ ed. Hawaiian Sugar Planters Assoc., Expt. Sta. Div. Path. Physiol. Bull. 5:163–195, 1906). In the intervening years, *Pasteuria* infections of virtually every known nematode have been observed, and their potential for use in biological control of phytopathogenic nematodes has been noted (Chen and Dickson [1998] *J. Nematology* 30:313–340).

The life cycle of the bacteria begins when endospores bind to the cuticle of the nematodes in soil. *P. penetrans* proliferates within the nematode body and passes through several documented morphological phases, including mycelial structures and thalli, culminating in the development of endospores. Endospores are released when the nematode body lyses. Growth of the bacteria within the nematode body reduces or eliminates the production of eggs by the nematode, severely restricting the rate of nematode reproduction. Economic damage to the host crop normally is inflicted by the first generation progeny of nematodes and is prevented by *Pasteuria* through lowering the concentration of progeny nematodes in the plant root zone.

Most of the experimental work with the *Pasteuria* group of bacteria has used endospores produced in live nematodes, cultivated on whole plants in greenhouses where aseptic conditions do not prevail. In two exceptions, Verdejo et al. (Verdejo, S. and R. Mankau [1986] *Journal of Nematology* 18:635) have reported on the oligoxenic culture of *Pasteuria penetrans* in live *Meloidogyne incognita* on excised tomato root culture; and Reise et al. (Reise, R. W., et al. [1988] Abstracts of the $27^{th}$ Annual Meeting Society of Nematologists, p. 75; Reise, R. W. et al. [1991] *J. Nematol.* 23:547–548) have studied factors in various tissue culture media affecting *Pasteuria* isolates from *Heterodera glycines*, *Meloidogyne incognita*, and *Pratylenchus brachyurus*. Their attempts are directed at a genuine in vitro cultivation of *Pasteuria*, which attempts fail on the basis of the fundamental criterion that a genuine in vitro cultivation of any prokaryotic organism must be marked by a continual survival and proliferation of the organisms, upon transfer to a fresh medium, at some definable growth rate that is characteristic of the genotype of the organism and the environmental conditions.

Previous attempts at culturing *P. penetrans* typically have relied on introducing vegetative cells from infected nematodes into selected culture media. These media included an extensive array of carbon and nitrogen sources, commercial growth media, extracts of other microorganisms or fungi, or tissue culture of nematode cells (Reise et al., 1988; Bishop and Ellar, 1991; Previc and Cox, 1992). However, sustained growth of *Pasteuria* was never observed in any of these media.

U.S. Pat. No. 5,094,954 describes an alternative method for producing endospores from *Pasteuria* by growing the bacteria on explanted nematode tissue. In the method of U.S. Pat. No. 5,094,954, the nematode tissue may be prepared, for example, by decapitating and decaudating nematodes, or by osmotic and/or enzymatic disruption of the nematode cuticle. The nematode tissue is explanted onto media which is designed to nourish the tissue and keep it in a metabolically active state. The tissue is then induced into growth and cell proliferation. Thus, this method does not rely on in vitro cultivation of the *Pasteuria*, but is directed at the production of *Pasteuria* endospores on explanted or cultured nematode tissue.

Thus, although *Pasteuria* was first reported as far back as 1888, all attempts to culture the microbe in vitro have failed to produce a viable means of producing endospores. Therefore, there remains in this art a great need for a method of producing *Pasteuria* by spore formation following true in vitro growth of the vegetative phase of *Pasteuria* on an artificial growth medium consisting of inexpensive, readily available materials. Such systems are not known at this time.

BRIEF SUMMARY OF THE INVENTION

The subject invention provides novel and advantageous methods for growing bacteria. In a preferred embodiment of the subject invention, *Pasteuria* endospores, such as those that infect the rootknot nematode *Meloidogyne arenaria* or other host nematodes, are grown in vitro. The methods of the subject invention are highly advantageous because *Pasteuria* can be grown in the absence of nematode tissue.

The culture methods of the present invention are at least partly based upon the surprising discovery that *Pasteuria* is an acidophilic parasite that grows best in acidic medium having a reduced dissolved oxygen concentration (compared to saturation with atmospheric oxygen).

The subject invention provides methods for the in vitro growth of *Pasteuria* using a culture medium that has an acidic pH. Preferably, the pH is less than about 6.0, more preferably the pH is less than about 5.5 and, most preferably, the pH is between about 3.0 and about 5.0. Particularly preferred culture media are buffered to maintain the desired pH. Agents that can be used to acidify the culture medium include, but are not limited to, hydrochloric acid, sulfuric acid, acetic acid, and other organic acids. Buffer systems that can be used include, but are not limited to, potassium hydrogen phthalate, acetic acid, succinic acid and citric acid.

Using the methods of the subject invention, in vitro growth of *Pasteuria* can be carried out under proper conditions using a variety of culture media.

In one embodiment of the method of the subject invention, *Pasteuria* is grown in the presence of a complex medium. Preferably, the complex medium is a synthetic medium that does not contain host materials, culture filtrate, or other extract from another organism.

Advantageously, the method of the subject invention results in growth of bacterial mass and an increase in the number of cellular units of the vegetative stage of the bacteria. Subsequently, sporulation occurs from the late vegetative phase of the bacteria with production of mature, dormant endospores. The endospores are infective for nematodes, including *Meloidogyne arenaria* and other nematode species.

Advantageously, the in vitro culture techniques of the subject invention can be used to efficiently grow *Pasteuria* isolates from a variety of nematodes, including *Pasteuria* sp. from *Belonolaimus* sp. (Sting), *Hopolaimus* sp. (Lance) and *Heterodera* sp. (Cyst) nematodes.

The endospores obtained using the methods of the subject invention can be used in any appropriate composition or process. Specifically exemplified herein is the production of *Pasteuria* endospores and the use of these endospores in nematode control programs.

The subject invention also concerns the *Pasteuria* culture media and in vitro *Pasteuria* cultures described herein.

BRIEF DESCRIPTION OF DRAWINGS

FIGS. 2A and 2B show mycelial balls in vivo and in vitro, respectively (Hatz, B. and Dickson, D. W. [1992] *J. Nematol.* 24:512–521). FIGS. 2C and 2D show thalli in vivo and in vitro, respectively (Chen, Z. X. et al. [1997] Phytopathology, 87:273–283). FIGS. 2E and 2F show mature endospores produced in vivo and in vitro respectively attached to the root-knot nematode in vivo and in vitro, respectively.

DETAILED DISCLOSURE OF THE INVENTION

Figure 1:
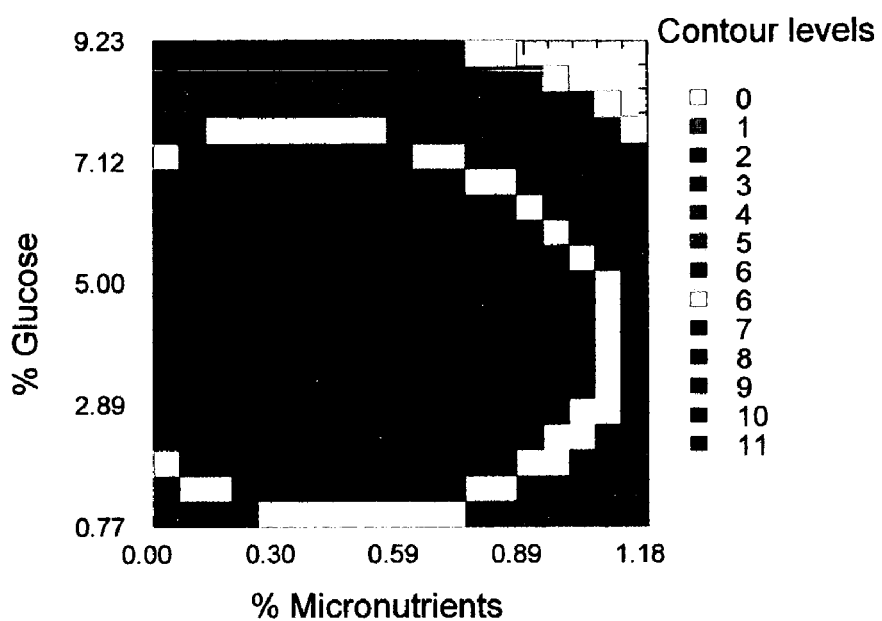
FIG. 1 shows response surface analysis (RSA) of glucose and micronutrients used to produce glucose-salts broth for production of *E. cloacae* culture filtrate. Response values are ranks of the total amount of *P. penetrans* biomass estimated in the various filtrates, observed after two weeks incubation at 30° C. Response values are plotted as function of % glucose and % micronutrients, and shown as a contour plot.

The subject invention provides methods for the efficient production of bacterial endospores. Specifically exemplified herein is the in vitro production of *Pasteuria* endospores. In accordance with the subject invention, *Pasteuria* are grown and produce endospores that have the advantageous property of being able to attach to, infect, grow in, re-sporulate in, reduce the fecundity of, and/or kill certain types of phytopathogenic nematodes.

In one aspect, the subject invention provides a method for producing endospores of parasitic bacteria species in vitro without the presence of living host tissue. In a preferred embodiment, the subject invention provides methods for the in vitro growth of *Pasteuria* using a culture medium which has an acidic pH. Preferably, the pH is less than about 6.0, more preferably the pH is less than about 5.5 and, most preferably, the pH is between about 3.0 and about 5.0. Specifically exemplified herein is culture media having a pH of about 4.0. Particularly preferred culture media are buffered to maintain the desired pH. Agents which can be used to acidify the culture medium include, but are not limited to, hydrochloric acid, sulfuric acid, acetic acid, and other organic acids. Buffer systems include, but are not limited to, potassium hydrogen phthalate, acetic acid, succinic acid and citric acid.

A further aspect of the subject invention concerns the growth of *Pasteuria* in a reduced medium having a lower dissolved oxygen concentration than that which results when the medium is saturated with atmospheric oxygen. Thus, for example, for a medium that has an oxidation-reduction potential (ORP) of about 220 mV when in equilibrium with atmospheric levels of oxygen, the method of the subject invention is best practiced if the dissolved oxygen concentration is reduced such that the medium has a ORP of less than about 200 mV and preferably below about 150 mV. In a preferred embodiment the ORP is between about 50 and 150 mV during vegetative growth. If desired, sporulation can be induced. In one embodiment, an increase of ORP to, for example, 150–200 mV has been found to induced sporulation.

The reduction in ORP can be achieved by, for example, adding thiolactic acid to the medium. In a preferred embodiment, fresh thiolactic acid is added on a regular basis as needed to counter the effects of re-oxidation that may occur at the surface of the medium where the medium contacts atmospheric oxygen.

In a specific embodiment, vegetative cells obtained from an infected nematode are introduced into a nutrient medium and grown. This growth can be carried out at room temperature. A standard nutrient broth, optionally supplemented, can be utilized. The nutrient broth may be supplemented with an egg yolk preparation, peanut oil, or other source of lipids, and/or lecithin.

In one embodiment of the process of the subject invention, the preparation can be transferred to a solid growth medium in, for example, a petri dish. Typically, within about 24 hours of growth in the nutrient medium, colonies will appear on the plates (petri dishes). After appearance of the colonies in the nutrient medium, induction of spore formation can be done by, for example, adding manganese sulfate and/or lipids.

Physical embodiments of the culture medium include, but are not limited to, liquid or solid, frozen, lyophilized or dried into a powder. In a preferred embodiment of the subject invention, the growth process is carried out to completion in liquid growth medium. This process is simple and highly efficient.

Production of endospores can then be induced as described herein. Endospores will typically form within about one week of spore induction. These endospores have been determined to be capable of attaching to J2 juvenile nematodes.

Using the methods of the subject invention, in vitro growth of *Pasteuria* can be carried out under acidic conditions using a variety of culture media, including defined and undefined media. The culture medium can contain a variety of amino acids, salts, carbohydrates, vitamins, and other supporting nutrients. For example, the culture medium can contain one or more of the following components: glucose, NaCl, yeast extract, $NH_4H_2PO_4$, $(NH_4)_2SO_4$, glycerol, valine, L-leucine, L-glutamine, L-alanine, L-valine, L-tyrosine, L-tryptophan, lactic acid, propionic acid, succinic acid, malic acid, citric acid, KH tartrate, vitamin solution, mineral solution, xylose, lyxose, and lecithin. Preferably, the culture medium contains one or more of the following components: lactic acid, propionic acid, succinic acid, malic acid, citric acid, tartaric acid, and yeast extract. More preferably, the culture medium contains one or more of the following components in the indicated concentrations: about 0.05 g/L of lactic acid, about 0.8 g/L to about 1.6 g/L of propionic acid, about 0.3 g/L to about 6.0 g/L succinic acid, about 2 g/L to about 4 g/L malic acid, about 3 g/L to about 6 g/L citric acid, about 3 g/L to about 6 g/L tartaric acid, and up to about 3 g/L yeast extract.

In one embodiment of the method of the subject invention, *Pasteuria* is grown in the presence of a complex medium. Preferably, the complex medium is a synthetic medium that does not contain host materials, culture filtrate, or other extract from another organism.

In accordance with the methods of the subject invention, it is possible to maintain *P. penetrans* in culture in vitro and observe all the classical structures described in the literature, including mycelial balls, thalli, and endospores. When fresh conditioned medium (CM) was supplied daily to cultures in tissue-culture plates, the cultures were observed to produce mycelial balls and other associated structures leading to sporulation over a period of approximately 90 days.

Endospores produced in vitro according to the subject invention were tested for attachment to nematodes and found to attach at rates comparable to endospores produced in vivo. Infectivity of these endospores was verified by inoculating nematodes with endospores attached onto tomato plants. Daughter endospores were found to have developed within the nematode bodies after approximately 500 degree days, which was comparable to the time required for in vivo endospores.

In addition to the classical structures described in the literature, the in vitro cultures also contain small structures resembling typical bacterial rods and cocci. These structures can be observed to increase in number and spread throughout the tissue culture wells.

The subject invention also includes the *Pasteuria* culture media disclosed herein and in vitro *Pasteuria* cultures disclosed herein. Preferably, the in vitro *Pasteuria* cultures of the subject invention comprise an acidic culture medium and *Pasteuria* endospores grown in vitro in the culture medium. More preferably, the culture medium contains no host nematode tissue.

As used herein, the terms "conditioned medium" and "CM" are intended to include filtrates and other extracts of *Enterobacter cloacae* culture.

In a preferred embodiment, of the subject invention *Pasteuria penetrans* is grown at about pH 4, lower dissolved oxygen concentration than that which is saturated with atmospheric oxygen levels and an oxidation-reduction potential (ORP) below about 150 mV in medium that displays an ORP of approximately 220 mV when in equilibrium with atmospheric levels of oxygen.

Fresh thiolactic acid can be added to cultures on a regular basis to reduce ORP levels, but this steadily re-oxidizes, from the surface of the solution down to the lowest levels of the culture dish. The thiolactic acid concentration, frequency of refreshing and culture medium depth were experimentally determined to provide the longest possible culture time with these variables optimized. Under these conditions, *Pasteuria* grows to very high concentrations in the center of the well, near the lower surface of the culture dish, presumably because this region stays at the appropriate ORP level for longer periods and is at lower dissolved oxygen levels than regions near the upper surface of the medium or near the sides of the culture well.

Sampling from this high growth region is deemed to be appropriate because on switching to *Pasteuria* culturing in bioreactors, it will be possible to achieve the desired oxygen concentration and ORP level throughout the entire bioreactor, thereby achieving optimum cell yield throughout.

The subject invention further provides bacterial endospore compositions useful for pest control. Specifically exemplified are endospore compositions of bacteria that are pathogenic to nematodes and grow in, or on, live nematode tissue. Such bacteria, including for example, *Pasteuria* sp. can be readily identified and isolated as described herein. For example, nematodes can be collected (from, for example, the roots of plants) and surface sterilized to remove bacteria that are not directly associated with the nematodes. The nematodes can then be popped open and their contents grown on culture media as described herein. The pathogenicity to nematodes of any bacteria that grow in these cultures can be confirmed by applying the bacteria to nematodes as described herein.

Advantageously, because nematode tissue is not needed to grow the endospores of the present invention, the commercial endospore preparations would not contain significant amounts of nematode tissue. On the other hand, the commercial preparation can contain components from the in vitro growth medium. Such components would be, for example, succinic acid and/or thiolactic acid.

The commercial preparation would have a high concentration of endospores, typically in excess of $1\times10^7$ spores/ml and preferably in excess of $1\times10^9$ spores per ml or gram of dry product.

In a preferred embodiment, the commercial product would include, on the package or accompanying the package, instructions for use of the product for pest control.

Advantageously, the subject invention can be practiced without growing the *Pasteuria* in contact with a culture of *E. cloacoe* (or any other "helper factor" as contemplated in WO 01/11017 A2, incorporated herein by reference) or a filtrate of a culture of a helpfer factor. Thus, the current invention is to be distinguished from, and is advanteous compared to, WO 01/11017 A2 because the critical chemical components and chemical characteristics of the culture media have been identified. Thus, the practice of the current invention does not require the methods explicitly described in WO 01/11017 A2 wherein a helper factor and/or filtrate obtained directly from a helper factor are introduced into the medium. Rather, the pH and/or ORP are modulated to the values described herein by addition to the media of defined components such as, for example, succinic acid and thiolactic acid.

As used herein, reference to in vitro growth medium excludes a medium comprising sufficient nematode tissue to support growth of bacteria. Reference here to "growth of bacteria" means growth that could yield sufficient numbers of bacteria to create a composition that could be used for pest control.

The endospores of the present invention can be used to control pests using methods well known to those skilled in the art. Specifically exemplified herein is the control of nematodes on plants. The plant may be for example, tomatoes and other vegetables, corn, or any other plant attacked by nematodes.

Reference herein to ORP values are based on a culture medium having an ORP of about 220 mV when saturated with atmospheric oxygen. For medium having a different saturated ORP, the reduction in ORP to achieve growth in accordance with the subject invention can be readily determined by a person skilled in the art having the benefit of the instant disclosure. This reduction would typically be, for example, at least about 20%.

Materials and Methods

In vivo culture of *P. penetrans*. *M. arenaria* Race 1 nematodes were attached to *P. penetrans* endospores via the centrifugation method (Hewlett and Dickson, 1993), so that 100% of the nematodes had 1 to 5 endospores bound. The nematodes were then applied to six-week-old tomato plants (*Lycopersicon esculentum* cv. Rutgers) and grown for 230 degree days, defined as the average Celsius temperature attained in each 24-hour period minus 18° C., then summed for total days of incubation (Serracin-Ulate, M. et al. [1997] *J. Nematol.* 29:228–238).

Collection of infected females. The root systems were rinsed thoroughly and root galls were excised with a scalpel after soaking the root for 2–3 hours in a solution of 20% Crystalzyme (VALLEY RESEARCH, South Bend, Ind.). Excised nematodes were rinsed in groups of five on a 5-micrometer sieve with 300 mL of sterile deionized water. After rinsing, small aliquots of the rinse water were plated onto nutrient agar to confirm that no more bacteria were being eluted from the nematode cuticle. Nematodes were then crushed on sterile glass cover slips and examined microscopically to confirm the presence of *P. penetrans* vegetative cells. Crushed nematodes were then transferred to various growth media and the cultures were observed daily.

Culture of *E. cloacae*. The motile, rod-shaped bacterium was isolated in pure culture as single colonies on nutrient agar plates. Preliminary identification was made by Gram stain (negative) and BBL Enterotube II (BECTON DICKINSON, Sparks, Md.). Final confirmation by DNA sequencing indicated the isolate was a strain of *Enterobacter cloacae* and has been deposited with the American Type Culture Collection (ATCC) and has been assigned accession no. PTA-2324. DNA of the 165 RDNA gene of *E. cloacae* is described in international publication WO 01/11017 (PCT application no. PCT/US00/21942), which is incorporated herein by reference in its entirety. This bacterium can be grown to turbidity in shake flasks in a simple glucose-salts broth and maintained cryogenically. Although other bacterial flora were isolated from these cultures, *E. cloacae* was both numerically dominant and repeatedly isolated from infected nematodes. Most of the additional flora did not produce conditions conducive to growth of *P. penetrans* and production of endospores.

Co-culture medium. The minimal glucose salts medium for co-culture consisted of 5% glucose, 1% egg yolk, 0.1% yeast extract and was supplemented at 5% with a saturated solution of Wesson's salts (SIGMA).

Complex Medium. The base medium consisted of the following components, with amounts in g/L: NaCl, 5; yeast extract, 1; $NH_4H_2PO_4$, 1; $K_2HPO_4$, 1; $(NH_4)_2SO_4$, 1.3; lactic acid, 0.05; propionic acid, 1.6; succinic acid, 6; malic acid, 4; citric acid, 6; potassium hydrogen tartrate, 6. In addition, 10 mL of minerals solution and 10 mL of vitamins solution were added per L. Minerals solution consisted of the following components, in g/L: $CUSO_4.5H_2O$, 0.97;

MnSO$_4$.4H$_2$O, 9.4; ZnSO$_4$, 3.2; H$_3$BO$_3$, 0.14; NH$_4$Mo, 0.026; FeSO$_4$, 0.49; EDTA, 1.2. A 100× vitamins solution consisted of the following components, in g/L: cobalamine (vitamin B12), 0.01; biotin, 0.2; thiamine HCl, 0.5; calcium pantothenate, 0.5; folic acid, 0.2; riboflavin, 0.5; nicotinamide, 0.9 and pyridoxine HCl, 1. This stock was diluted 1:100 and used as described above. The base medium was then supplemented with glucose and pH was adjusted to the levels indicated in the figure. The same base medium formulation was used for medium development experiments with *Belonolaimus longicaudatus* and *Hoplolaimus* sp. nematodes in which pH and glucose were varied (Example 7).

Following are examples which illustrate procedures for practicing the invention. These examples should not be construed as limiting. All percentages are by weight and all solvent mixture proportions are by volume unless otherwise noted.

EXAMPLE 1

Preparation of Nematodes and Growth of *Pasteuria* in Co-culture with *Enterobacter cloacae*

Infected Rootknot (*Meliodogyne arenaria*) females were surface washed in autoclaved water. Approximated 100 ml of water were passed over the nematodes in a fine mesh screen. These nematodes were then crushed between autoclaved glass slides in a drop of water. The suspension of material was inoculated into 24 well, sterile plates which contained sterile insect cell culture media (0.5% glucose and Leibovitz) with 5% Bovine Calf Serum (BCS) added. Growth was observed within 24 hours at room temperature. The growth consisted of motile rods, which was not expected. This material was observed for several days and a few refractile bodies resembling *Pasteuria* mycelial balls appeared. When stained with Gram's Stain the culture contained both negative and positive material. The structures resembling mycelial balls were Gram positive.

Material from agar plates was inoculated into nutrient broth (NB) with BCS. Within 24 hours abundant growth was evident including structures that appeared to be identical to structures found in infected nematodes. In several days, refractile bodies also appeared.

EXAMPLE 2

Choice of Medium for Co-culture

Nutrient broth (NB) and 0.5% glucose can be used as the media. Endospores produced in the NB attached more readily to the J2's than those produced in 0.5% glucose. A sterile egg yolk preparation was added to the NB and endospores were produced. This media contained 5% BCS and 5% egg yolk mixture. The endospores attached to the J2's.

The NB media containing the egg yolk and salts was diluted 1:1, 1:5 and 1:10. In all cases growth and endospores were obtained. One percent glucose was used with the egg yolk and salts and good growth and endospores were obtained.

Subsequently, it was determined that the egg yolk mixture could be reduced and that dried egg yolk could be used. Additional media include NB (8 g/l) or Glucose (10 g/l) plus 2.5% egg yolk and 5% saturated Wesson Salts. The richness of these media can be reduced if desired.

The tomato experiment was repeated and in all cases female root knot nematodes were recovered which were filled with *Pasteuria penetrans* endospores.

EXAMPLE 3

Production of *E. cloacae* Filtrate

*E. cloacae* (ATCC deposit number PTA 2324) was grown to turbidity in glucose salts broth containing 2 g/L glucose, 1 g/L each of ammonium dihydrogen phosphate and dipotassium phasphate, 5 g/L NaCl, 0.2 g/L magnesium sulfate, 10 mL sterile liquid egg yolk (all obtained from SIGMA), and 0.8 g/L Essential Minor Elements (SOUTHERN AG INSECTICIDES, Palmetto, Fla.) as a source of trace metals. After 48 hours at 35° C., the bacteria were removed from the culture medium with a 0.2 μm filter. The resulting filtrate was used to supplement various commercial growth media for support of *P. penetrans* as well as a stand-alone growth medium.

The glucose concentration used in producing the filtrate via *E. cloacae* metabolism was optimized by Response Surface Analysis (RSA; NCSS, Jun. 7, 2001, release, NCSS STATISTICAL SOFTWARE, Kaysvile, Utah). FIG. 1 shows RSA data on *E. cloacae* filtrate presented as a contour plot. Table 1 and Table 2 are the experimental data set for the contour plot of FIG. 1. Structures observed in vitro were comparable to those produced in vivo, as shown in FIG. 2.

TABLE 1

Growth Response of Pasteuria to Glucose and Micronutrients.

| % Glucose | % Micronutrients | Rank of total growth observed |
|---|---|---|
| 2 | 0.1 | 8 |
| 2 | 1 | 7 |
| 8 | 0.1 | 6 |
| 8 | 1 | 3 |
| 0.8 | 0.6 | 5 |
| 9.2 | 0.6 | 0 |
| 5 | 0 | 7.5 |
| 5 | 1.2 | 3.5 |
| 5 | 0.6 | 8 |
| 5 | 0.6 | 10 |
| 5 | 0.6 | 10 |
| 5 | 0.6 | 11 |
| 5 | 0.6 | 11 |

EXAMPLE 4

Growth and Development in *E. cloacae* Filtrate

When fresh *E. cloacae* culture filtrate was supplied daily to *P. penetrans* cultures in tissue-culture plates, the cultures were observed to produce mycelial balls, thalli and other associated structures leading to sporulation over a period of approximately 90 days. Endospores produced in vitro were tested for attachment to nematodes and were found to attach at rates comparable to endospores produced in vivo. Infectivity of these endospores was verified by allowing the endospores to attach to nematodes and then inoculating the nematodes onto tomato plants. Daughter endospores were found to have developed within the nematode bodies after 500 degree days, which was comparable to the time required for in vivo endospores.

In addition to the structures already described in the literature, the in vitro cultures also contained small structures resembling typical bacterial rods and cocci. These structures were observed to increase in number and spread throughout the tissue culture wells. They may represent a previously undocumented phase of *P. penetrans* growth, especially since they were frequently observed in close association with developing mycelial balls over time. They did not grow on agar plates made from nutrient broth, brain-heart infusion, mannitol salts, MacConkey broth or a low-pH agar for moderate acidophiles. PCR analysis employing *P. penetrans* specific primers was positive on these samples, while PCR with universal bacterial primers or nematode primers were negative, indicating the absence of *E. cloacae* or nematode cells (Duan et al. manuscript submitted for publication).

EXAMPLE 5

Analysis of *E. cloacae* Filtrate

Additional observations of the filtrate included a distinctive sour odor. This was indicative of the production of organic acids by *E. cloacae*, a well-documented phenomenon (Brock T. D. and Madigan, M. T., in Biology of Microorganisms, $6^{th}$ Edn., pp. 707–790, Prentice-Hall, Englewood Cliffs, N.J., 1991). The production of these acids would tend to significantly lower the pH of the poorly-buffered glucose salts broth, and the filtrate was found to have a typical pH of 3.4+/−0.4.

High-pressure liquid chromatography (HPLC) analysis showed that a range of typical fermentation products were present in the filtrate, including the expected organic acids (succinic, malic, citric, tartaric and lactic). The filtrate was also found to contain a significant residual glucose concentration, as measured by a glucose oxidase assay (SIGMA).

The filtrate was found to no longer support *P. penetrans* growth after storage for 3 to 5 days at 4° C., indicating the presence of a labile component essential to the organism. Preliminary experiments to identify this component used a second filtration through a membrane with a 10,000 MWCO value. Filtrate passed through this membrane had equal success in supporting *P. penetrans* growth as the primary filtrate, indicating the essential component(s) were relatively small molecules.

EXAMPLE 6

Complex Medium Development Using Response Surface Analysis

Figure 3:
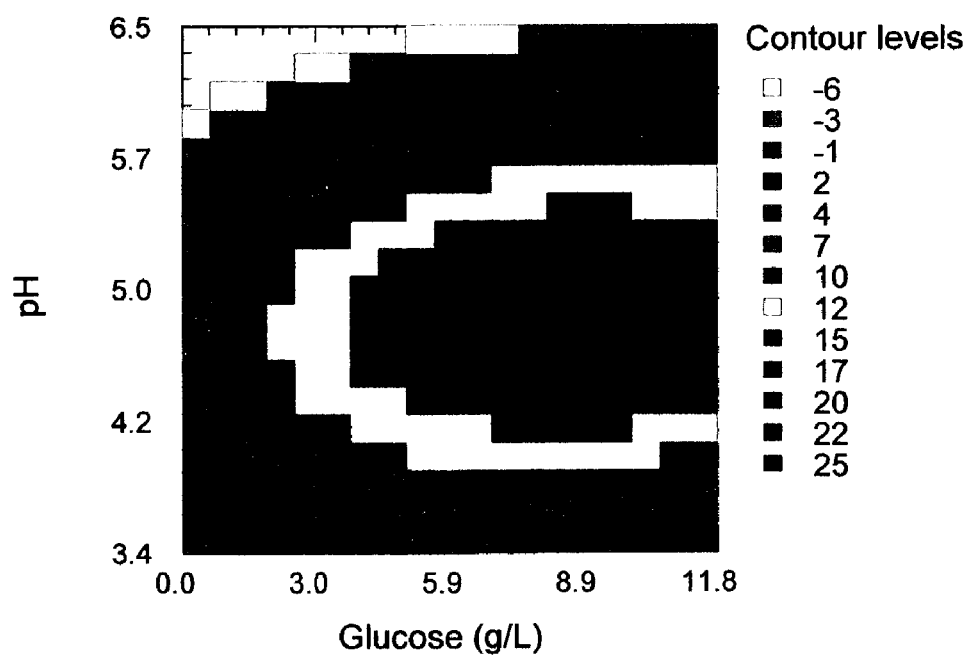
FIG. 3 shows the growth response of *P. penetrans* to glucose and pH in complex media, evaluated by RSA. Response values are the difference in mycelial ball counts after three days incubation at 30° C. The mycelial ball counts were performed on a transect at 400× magnification, through a well of a 24-well tissue culture plate. Since mycelial ball production is correlated with growth, the largest differences indicate regions of conditions most conducive to growth in culture. Response values are plotted as a function of pH and glucose (g/L), and shown as a contour plot.
Figure 2A:
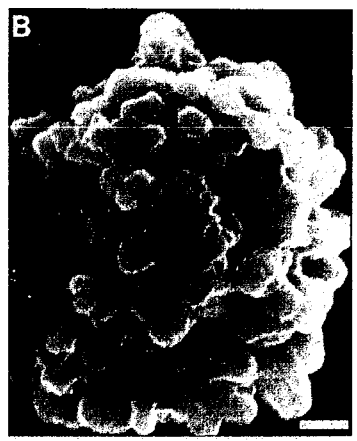
FIGS. 2A–2F show SEM and light microscopic images comparing *Pasteuria* structures in vivo and in vitro.
Figure 2B:
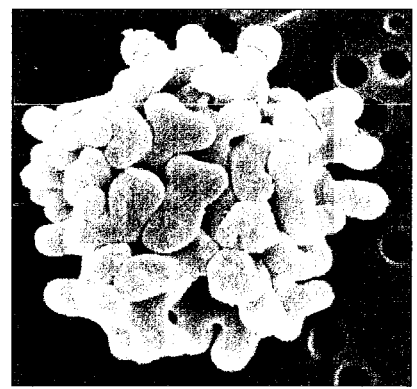
Figure 2C:
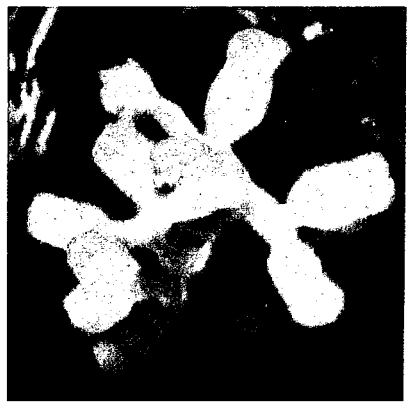
Figure 2D:
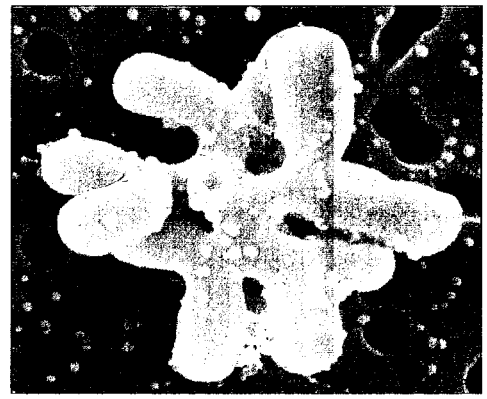
Figure 2E:
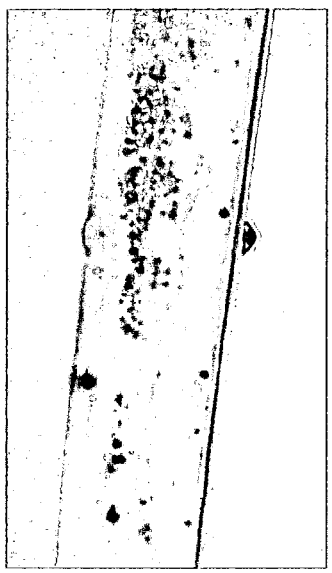
Figure 2F:
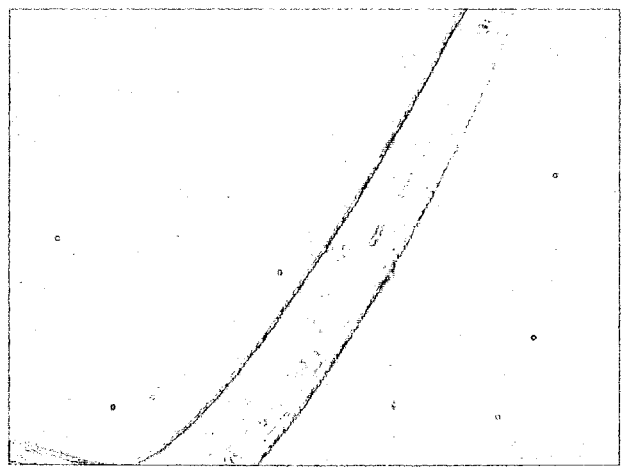

Complex medium was developed based on observations of the composition of the *E. cloacae* filtrate. Phthalic acid was chosen as the buffer system because of its pK's in the region of interest (2.89 and 5.51) and organic acids were added to concentrations similar to those observed by HPLC analysis of filtrate. FIG. 3 shows the growth response of *P. penetrans* at glucose concentrations varying from 0 to 11.9 g/L and at pH's from 3.8 to 6.0, presented as a contour plot. Optimal growth was observed for a pH of approximately 5 and a glucose concentration of just under 6 g/L. Table 2 is the experimental data set for the contour plot of FIG. 3.

TABLE 2

Growth Response of *P. penetrans* to Glucose and pH in Complex Medium.

| PH | Glucose (g/L) | Difference in mycelial ball counts |
|---|---|---|
| 3.8 | 1 | 4 |
| 3.8 | 10 | 10 |
| 6 | 1 | −7 |
| 6 | 10 | 3 |
| 3.4 | 5.5 | −1 |
| 6.5 | 5.5 | −4 |
| 4.9 | 0 | 7 |
| 4.9 | 11.9 | 16 |
| 4.9 | 5.5 | 7 |
| 4.9 | 5.5 | 17 |
| 4.9 | 5.5 | 13 |
| 4.9 | 5.5 | 13 |
| 4.9 | 5.5 | 26 |

EXAMPLE 7

Culture of *Pasteuria* from Other Nematode Species

Figure 4:
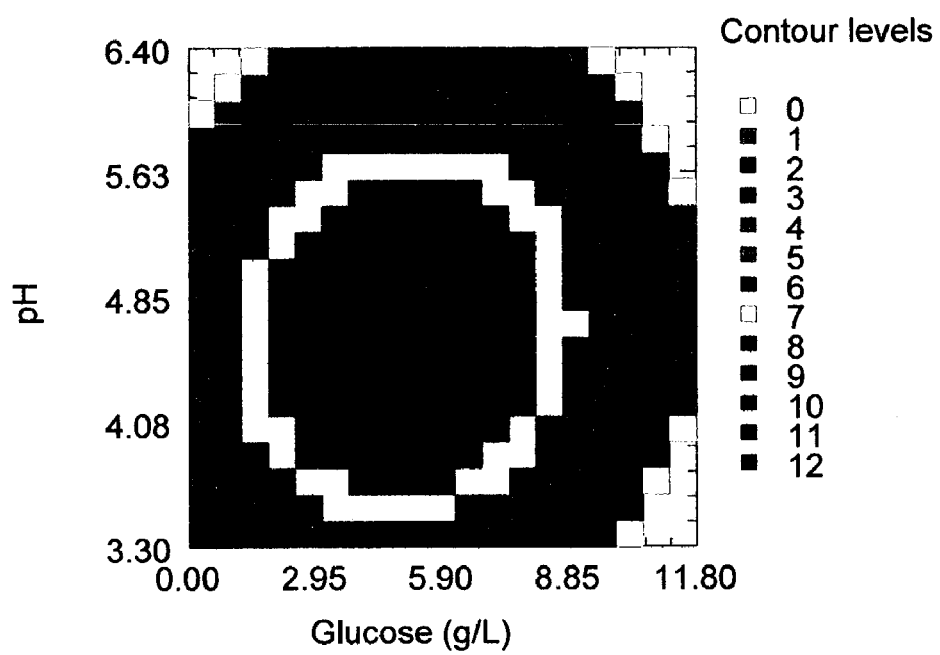
FIG. 4 shows the growth response of *Pasteuria* sp. from the Lance nematode to glucose and pH in complex media, evaluated by RSA. Response values are the difference in mycelial ball counts after three days of incubation at 30° C. The mycelial ball counts were performed on a transect at 400× magnification, through a well of a 24-well tissue culture plate. Response values are plotted as a function of pH and glucose (g/L), and shown as a contour plot.
Figure 5:
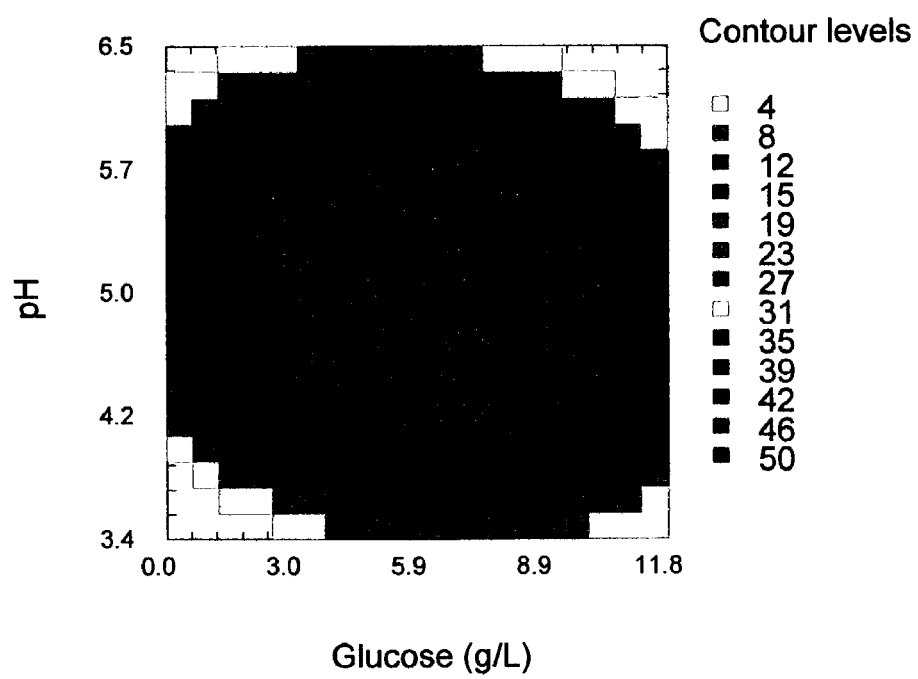
FIG. 5 shows the growth response of *Pasteuria* sp. from the sting nematode to glucose and pH in complex media, evaluated by RSA. The mycelial ball counts were performed on a transect at 400× magnification, through a well of a 24-well tissue culture plate. Response values are plotted as a function of pH and glucose (g/L), and shown as a contour plot.

*Hoplolaimus* sp. (lance nematodes) with *Pasteuria* endospores visible on their cuticle were sorted from soil samples and surface sterilized with a dilute sodium hypochlorite solution. The nematodes were then disrupted in various complex media and significant *Pasteuria* growth was noted. The glucose optimum was approximately 5 g/L and optimum pH was approximately 4.5, with a relatively broad peak of growth as a function of pH, as shown in FIG. 4. This result, along with similar results for growth of *Pasteuria* from *Belonolaimus longicaudatus* (sting nematode), as shown in FIG. 5, suggests that acid media are likely to enable growth of most *Pasteuria* species. Table 3 is the experimental data set for the contour plot of FIG. 4. Table 4 is the experimental data set for the contour plot of FIG. 5.

Figure 6:
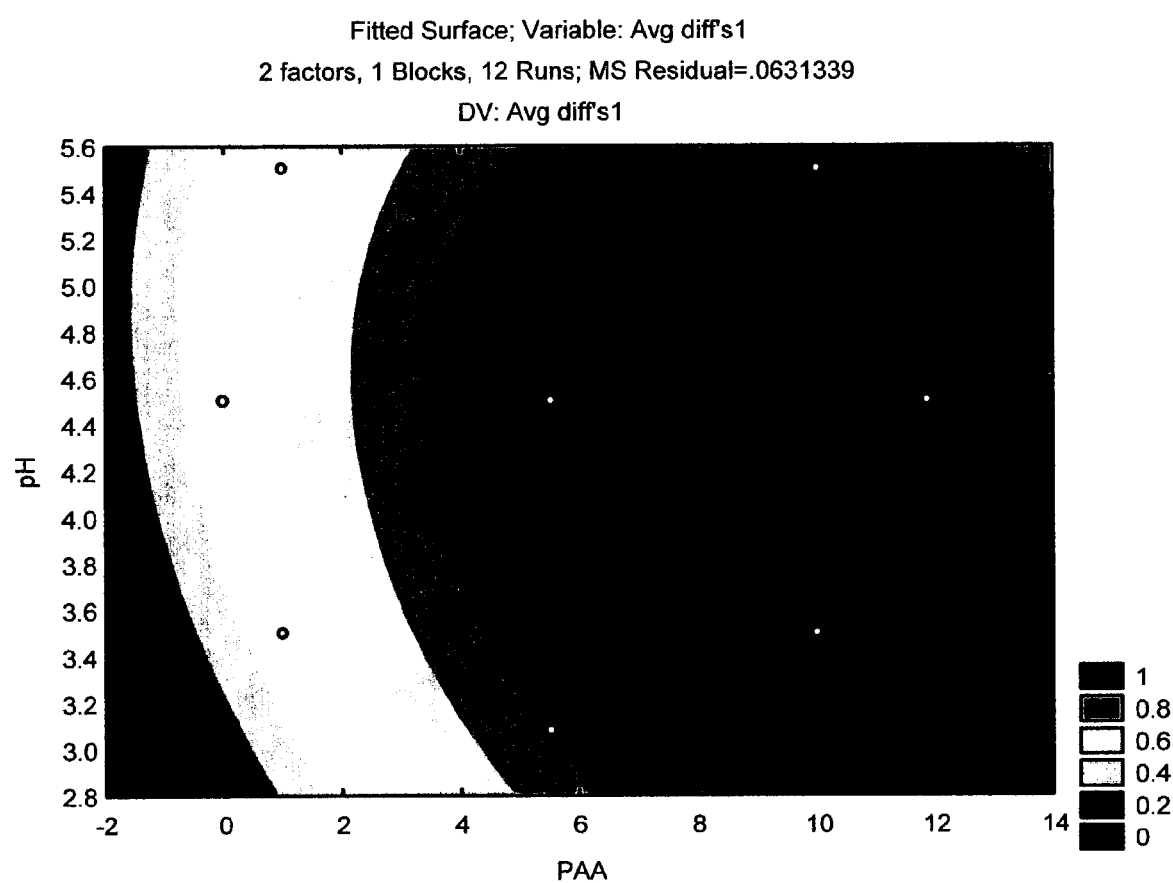
FIG. 6 shows the growth response of *Pasteuria* from Sting nematode to phenylacetic acid and pH in complex media, evaluated by response surface analysis. Response values are the difference in mycelial ball counts after three days of incubation at 30° C. Since mycelial ball production is correlated with growth, the largest differences indicate regions of conditions most conducive to growth in culture. Response values are plotted as a function of phenylacetic acid (PAA) and glucose (g/L), and shown as a contour plot.

FIG. 6: Growth Response of *Pasteuria* from Sting nematode to phenylacetic acid and pH in complex media, evaluated by response surface analysis. Response values are the difference in mycelial ball counts after three days of incubation at 30° C. Since mycelial ball production is correlated with growth, the largest differences indicate regions of conditions most conducive to growth in culture. Response values are plotted as a function of phenylacetic acid (PAA) and glucose (g/L), and shown as a contour plot.

TABLE 3

Growth Response of Pasteuria from Lance Nematode to Glucose and pH.

| pH | Glucose (g/L) | Difference in mycelial ball counts |
|---|---|---|
| 3.8 | 1 | 1 |
| 3.8 | 10 | 2 |
| 6 | 1 | 0 |
| 6 | 10 | 3 |
| 3.4 | 5.5 | 9 |
| 6.5 | 5.5 | 2 |
| 4.9 | 0 | 9 |
| 4.9 | 11.9 | 0 |
| 4.9 | 5.5 | 8 |
| 4.9 | 5.5 | 8 |
| 4.9 | 5.5 | 8 |
| 4.9 | 5.5 | 12 |
| 4.9 | 5.5 | 9 |

TABLE 4

Growth Response of Pasteuria from Sting Nematode to Glucose and PH.

| pH  | Glucose (g/L) | Difference in mycelial ball counts |
|-----|---------------|------------------------------------|
| 3.8 | 1             | 2                                  |
| 3.8 | 10            | 11                                 |
| 6   | 1             | 5                                  |
| 6   | 10            | 7                                  |
| 3.4 | 5.5           | 6                                  |
| 6.5 | 5.5           | 10                                 |
| 4.9 | 0             | 12                                 |
| 4.9 | 11.9          | 15                                 |
| 4.9 | 5.5           | 8                                  |
| 4.9 | 5.5           | 45                                 |
| 4.9 | 5.5           | 3                                  |
| 4.9 | 5.5           | 52                                 |
| 4.9 | 5.5           | 9                                  |

EXAMPLE 8

Growth of Different Isolates on Various Media

Figure 7:
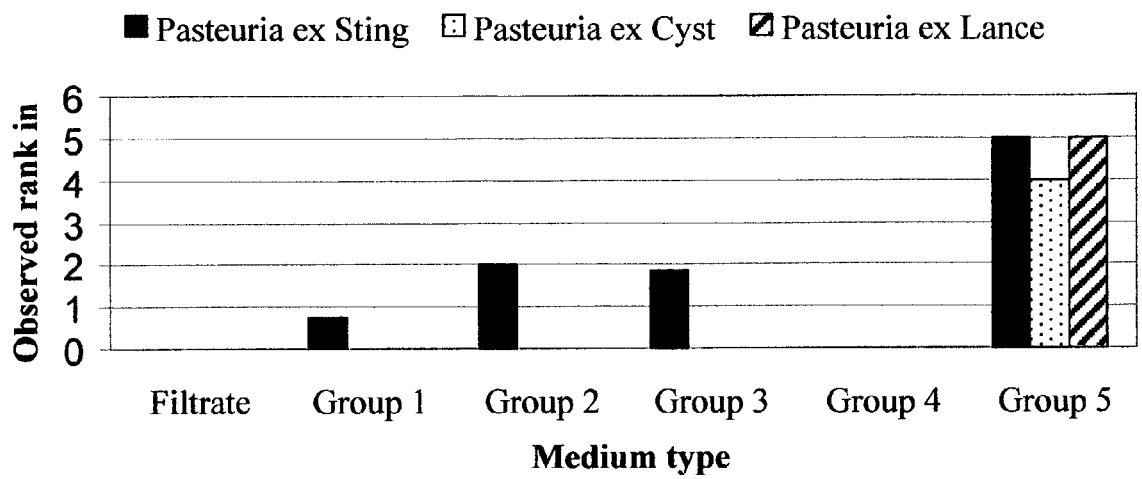
FIG. 7 shows growth of *Pasteuria* isolated from Sting, Cyst and Lance nematodes in various medium groups. The major component changes from one medium group to another are summarized in Example 8. Growth is rated on a numerical scale based on a qualitative evaluation of the culture.
Figure 8:
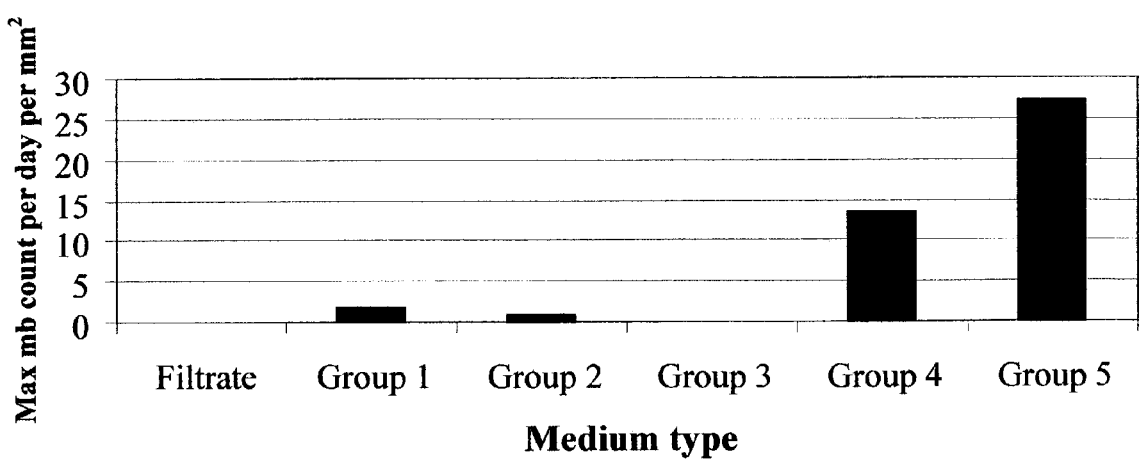
FIG. 8 shows growth of *Pasteuria penetrans* isolated from *M. arenaria* in the same medium groups as for FIG. 1. Actual growth rates, measured as the maximum mycelial ball count per day per square millimeter are given.

FIGS. 7 and 8 depict results for growth of various *Pasteuria* species. FIG. 7 shows growth of *Pasteuria* isolated from Sting, Cyst and Lance nematodes, with results grouped into five major media groups. In FIG. 8, analogous results are shown for *P. penetrans* from *M. arenaria* for comparison. Although the y-axes differ in the two figures, it is readily apparent that growth rates for all *Pasteuria* isolates analyzed respond similarly to the overall improvements that have been made in the culture medium and that each species of *Pasteuria* analyzed is amenable to the culture system of the subject invention.

The medium groups are as follows: "Filtrate" refers to *E. cloacae* filtrate as the growth medium; "Group 1" uses mixtures of organic acids and relied on various sugar sources; "Group 2" uses succinic acid, soy oil and lecithin with various protein sources; "Group 3" used succinic acid, a lipid emulsion system and various protein sources; "Group 4" has an improved organic acid mix, lipid emulsion and fat soluble vitamins; and "Group 5" adds phenylacetic acid, cyclohexane carboxylic acid, various proteins and various antioxidants.

EXAMPLE 9

Specific Medium

| x92–93 *P. penetrans* growth medium | |
|---|---|
| Component | g/L |
| NaCl | 1 |
| Meat peptone (Marcor Type D or Type EXP) | 18 |
| (NH4)H2PO4 | 0.75 |
| K2HPO4 | 0.75 |
| (NH4)2SO4 | 1 |
| Succinic acid | 25.7 |
| Whey | 0.23 |
| Minerals 92–83 | 8 mL |
| Vitamins | 8 mL |
| dH2O | 979 mL |

Mix above ingredients, madjust to pH=4 and filter sterilize. Then add aseptically:

| | |
|---|---|
| Soybean oil/lecithin emulsion with fat-soluble vitamins | 5 mL |

| Minerals 92-83 | g/L |
|---|---|
| CuSO4 | 0.07 |
| ZnSO4 | 6.4 |
| H3BO3 | 0.14 |
| NH4MoO4 | 6.E−04 |
| MgSO4 | 20 |
| EDTA | 1.2 |
| dH2O | 1000 mL |

| Vitamins | g/L |
|---|---|
| Cobalamin | 1.E−04 |
| Biotin | 2.E−03 |
| Thiamin HCl | 5.E−03 |
| Ca-pantothenate | 5.E−03 |
| Folic acid | 2.E−03 |
| Riboflavin | 5.E−03 |
| Nicotinamide | 9.E−03 |
| dH2O | 1000 mL |

| Soybean oil/lecithin emulsion with fat-soluble vitamins | g/100 mL |
|---|---|
| Soybean oil | 0.6 |
| Liquid soy lecithin | 0.06 |
| Vitamin K1 | 0.004 |
| Vitamin E | 0.004 |
| Cofactor Q10 | 0.001 |
| dH2O | 100 mL |

EXAMPLE 10

Sporulation

Primary isolate number 239.9 was prepared from tomato plant number 1069 at 216 degree days of nematode development on the plant. A total of 50 infected females were harvested from the plant, surface sterilized with hydrogen peroxide, and lysed in medium 88-57-2 (succinic acid at 25.7 g/L; NaCl at 5 g/L; yeast extract at 1 g/L; phenyl acetic acid at 0.8 g/L; whey protein at 2.4 g/L; fish peptone at 2 g/L; mineral mix* at 10 mL/L; vitamin mix at 10 mL/L; lipid emulsion* at 5 mL/L; thiolactic acid at 1 mM and superoxide dismutase at 1 U/mL; filter sterilized). The 50 lysed females were distributed to a total of 32 wells in 24 well culture plates at 2 mL per well. Additional components were added to the wells to construct a fractional factorial design for medium components in which a total of 13 components were analyzed. In addition to those above, a salt mixture, NZ Amine AS, potassium nitrate, meat peptone and yeast extract retentate were evaluated.

Cultures were established and wells were examined for number of cells and number of mycelial balls on Day 3 and again on Day 10. On Day 24, the cultures were transferred to 6 well culture plates, with approximately 6 wells from the 24 well plates being consolidated into one well per 6 well plate. At transfer, the medium was changed to 88-81-M (1 g/L NaCl; 8 mL/L mineral mix; 8 mL/L vitamin mix; 18 g/L meat peptone; 0.75 g/L $NH_4H_2PO_4$; 0.75 g/L $K_2HPO_4$; 1 g/L $(NH_4)_2SO_4$; 26 g/L succinic acid; 0.24 g/L whey protein; 5 mL/L lipid emulsion; adjusted to pH 4 and filter sterilized) and supplemented every two to eight hours with 2 mM thiolactic acid and 3 U/mL superoxide dismutase.

On Day 46 a 20 μL sample was withdrawn from the region of a 6 well plate with the highest concentration of sporulated *Pasteuria*, based on microscopic observation. This sample was diluted to 1 mL with sterile deionized water and was then subjected to sonication for one minute at 15 watts on a Fisher Sonic Dismembrator Model 60. The spore density was determined on a hemacytometer.

Raw hemacytometer counts for the culture were 28 spores and 27 spores on two samples. Converting from raw counts to spores per mL is achieved by multiplying by 10,000 to correct for the volume of material in the hemacytometer counting chamber and multiplying by 50 to correct for the dilution of the original sample. These two raw counts then convert to $1.4\times10^7$ spores per mL and $1.35\times10^7$ spores/mL. Averaging and allowing only two significant figures gives a final value of $1.4\times10^7$ spores per mL.

| *Mineral mix: | g/L (filter sterilized) |
| --- | --- |
| $CuSO_4.5H_2O$ | 0.73 |
| $MnSO_4.H_2O$ | 9.4 |
| $ZnSO_4$ | 3.2 |
| $H_3BO_3$ | 0.14 |
| $NH_4Mo$ | 0.026 |
| $FeSO_4.7H_2O$ | 0.42 |
| $MgSO_4$ | 20 |
| EDTA | 1.2 |
| **Vitamin mix: | g/L (filter sterilized) |
| Cobalamin (B12) | 0.001 |
| Biotin | 0.02 |
| Thiamine HCl | 0.05 |
| Ca-pantothenate | 0.05 |
| Folic acid | 0.02 |
| Riboflavin | 0.05 |
| Nicotinamide | 0.09 |
| ***Lipid emulsion | g/L |
| Soybean oil | 6 |
| Liquid lecithin | 0.6 |
| Vitamin K | 0.004 |
| Vitamin E | 0.004 |
| Vitamin Q10 | 0.001 |

To prepare emulsion, water is heated to 70° C. and the lipid-vitamin mixture is added dropwise with vigorous mixing. The emulsion is prepared as a 5 fold concentrate and then diluted prior to autoclaving.

EXAMPLE 11

Pot Trials

In vivo spores were grown on *Meloidogyne arenaria* Race 1 nematodes on tomato plants (Rutgers cultivar). Spores were harvested from root systems at 600 degree days after introduction of infected juvenile nematodes to the root systems of 3 to 4 week-old plants. In vitro spores were harvested from a number of culture experiments in which culture medium and culture methods had been developed. In all cases, cultures were established from M.a. females at no more than 220 degree days of development on plants. In many cases, material from several culture experiments was pooled and treated with media and methods intended to promote sporulation. Sporulated cultures were rinsed from the culture dish and the pooled material was subjected to sonication in a Fisher Sonic Desmembrator Model 60 with the output set to 15 watts for a 60 second treatment. Sonicated cultures were then centrifuged at 4000×g for 5 minutes and the pellets were rinsed at least once in sterile deionized water prior to resuspension in sterile deionized water. Spore concentrations for both in vivo and in vitro preparations were determined with the use of a hemacytometer.

Treatments were replicated five times in a completely randomized block design. Arendondo fine sand (95, 2.5, 2.5: sand, silt and clay) was inoculated with *Pasteuria* endospores at a rate of 100,000 endospores/cc, thoroughly mixed and allowed to air-dry on a tray for 24 hours. Twenty-five cc's of spore-treated soil were placed into 50 mL centrifuge tubes. M.a. juveniles, 1–5 days old collected from greenhouse culture were inoculated into each tube, 500 juveniles/tube in a 2 ml water suspension. Tomato seedlings, 3–4 week old, were transplanted into each pot. The treatments were as follows:

TABLE 5

| Treatment | Spore/cc of soil | Number of juveniles inoculated |
| --- | --- | --- |
| In vitro produced spores | 100,000/cc | 500 |
| In vivo produced spores | 100,000/cc | 500 |
| Untreated control | 0 | 500 |

Plants were incubated at 30° C. with a 16-hour day: 8-hour night schedule and checked daily for watering. Plants were rotated often in the incubator in an attempt to limit position effects in the incubator.

After 396 degree days root systems of all plants were washed clean and the following data collected:

Number of galls/root system

Number of egg masses/root system

Number of eggs/root system

% of 20 females collected from each root system infested with *Pasteuria*

The results obtained are shown in the Tables below:

TABLE 6

Number of Galls

| Replicate | Healthy plant control | Plants with nematodes No spores | In Vitro | In Vivo |
| --- | --- | --- | --- | --- |
| 1 | 0 | 21 | 33 | 5 |
| 2 | 0 | 8 | 27 | 25 |
| 3 | 0 | 14 | 1 | 22 |
| 4 | 0 | 9 | 0 | 35 |
| 5 | 0 | 28 | 7 | 5 |
| Mean | 0 | 16 | 13.6 | 18.4 |
| Std dev | 0.00 | 8.46 | 15.36 | 13.15 |

TABLE 7

Egg Masses

| Replicate | Healthy plant control | Plants with nematodes No spores | In Vitro | In Vivo |
| --- | --- | --- | --- | --- |
| 1 | 0 | 4 | 26 | 0 |
| 2 | 0 | 4 | 5 | 19 |
| 3 | 0 | 8 | 0 | |
| 4 | 0 | 2 | 0 | 29 |
| 5 | 0 | 45 | 3 | 0 |
| Mean | 0 | 12.6 | 6.8 | 12 |
| Std dev | 0.00 | 18.24 | 10.94 | 14.45 |
| % Reduction vs. untreated | | | 46.03 | 4.76 |

TABLE 8

Total Eggs

| Replicate | Healthy plant control | Plants with nematodes No spores | In Vitro | In Vivo |
|---|---|---|---|---|
| 1 | 0 | 363 | 1092 | 0 |
| 2 | 0 | 900 | 225 | 1950 |
| 3 | 0 | 722 | 0 | 420 |
| 4 | 0 | 483 | 0 | 2352 |
| 5 | 0 | 8125 | 52.5 | 0 |
| Mean | 0 | 2118.6 | 273.9 | 944.4 |
| Std dev | 0.00 | 3364.14 | 466.57 | 1123.76 |
| % Reduction vs untreated | | | 87.07 | 55.42 |

TABLE 9

Percent infected females

| Replicate | Healthy plant control | Plants with nematodes No spores | In Vitro | In Vivo |
|---|---|---|---|---|
| 1 | na | 0 | 35 | 0 |
| 2 | na | 0 | 20 | 60 |
| 3 | na | 0 | na | 0 |
| 4 | na | 0 | 0 | 0 |
| 5 | na | 0 | 0 | 0 |
| Mean | na | 0 | 13.75 | 16 |
| Std dev | na | 0 | 17.02 | 26.08 |

Reduction of egg masses is greater for in vitro spores, at 46% reduction, than for in vivo spores, at only 5% reduction.

Reduction for in vitro spores was 87% and for in vivo spores was only 55%, so as with the egg mass data, in vitro spores performed better than in vivo spores in this evaluation.

Additional Observations Recorded:

TABLE 10

Height Measurements (cm)

| Replicate | Healthy plant control | Plants with nematodes No spores | In Vitro | In Vivo |
|---|---|---|---|---|
| 1 | 10.5 | 3.5 | 11.2 | 11.2 |
| 2 | 10.2 | 10 | 11.2 | 8 |
| 3 | 12.2 | 9.8 | 4.2 | 10.8 |
| 4 | 11.3 | 10.2 | 7 | 7.2 |
| 5 | 13.8 | 10.9 | 10.8 | 7.3 |
| Mean | 11.6 | 8.88 | 8.88 | 8.9 |
| Std dev | 1.45 | 3.04 | 3.16 | 1.95 |

TABLE 11

Vigor Ratings

| Replicate | Healthy plant control | Plants with nematodes No spores | In Vitro | In Vivo |
|---|---|---|---|---|
| 1 | 9 | 5 | 9 | 9 |
| 2 | 9 | 7 | 9 | 8 |
| 3 | 9 | 7 | 6 | 8 |
| 4 | 10 | 8 | 7 | 7 |
| 5 | 10 | 9 | 8 | 7 |
| Mean | 9.4 | 7.2 | 7.8 | 7.8 |
| Std dev | 0.55 | 1.48 | 1.30 | 0.84 |

TABLE 12

Plant Wt (g)

| Replicate | Healthy plant control | Plants with nematodes No spores | In Vitro | In Vivo |
|---|---|---|---|---|
| 1 | 1.28 | 0.95 | 1.44 | 1.27 |
| 2 | 1 | 1.35 | 1.85 | 1.4 |
| 3 | 1.23 | 1.02 | 0.58 | 1.29 |
| 4 | 1.32 | 1.11 | 0.68 | 1.23 |
| 5 | 1.19 | 1.26 | 1.53 | 0.71 |
| Mean | 1.204 | 1.138 | 1.216 | 1.18 |
| Std dev | 0.12 | 0.17 | 0.56 | 0.27 |

TABLE 13

Root Wt (g)

| Replicate | Healthy plant control | Plants with nemartodes No spores | In Vitro | In Vivo |
|---|---|---|---|---|
| 1 | 0.38 | 0.33 | 0.42 | 0.41 |
| 2 | 0.35 | 0.5 | 0.57 | 0.47 |
| 3 | 0.41 | 0.37 | 0.17 | 0.52 |
| 4 | 0.55 | 0.38 | 0.24 | 0.54 |
| 5 | 0.54 | 0.49 | 0.69 | 0.32 |
| Mean | 0.446 | 0.414 | 0.418 | 0.452 |
| Std dev | 0.09 | 0.08 | 0.22 | 0.09 |

All patients, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for producing *Pasteuria* endospores in vitro, wherein said method comprises introducing bacteria *Pasteuria* into a growth medium that is free of sufficient nematode tissue to support bacterial growth, wherein the pH of said growth medium is less than about 6.0, and growing said bacteria *Pasteuria*.

2. The method, according to claim 1, wherein said medium is buffered to maintain a pH of less than about 6.0.

3. The method, according to claim 1, wherein the pH is maintained using a succinate buffer system.

4. The method, according to claim 1, wherein the oxidation reduction potential of said medium is reduced compared to the oxidation reduction potential when the medium is saturated with atmospheric oxygen.

5. The method, according to claim 1, wherein the oxidation reduction potential is between about 50 and about 200 mV.

6. The method, according to claim 1, wherein the medium further comprises peptone as a carbon and nitrogen source.

7. The method, according to claim 1, wherein the medium comprises the following components: meat peptone, succinic acid, zinc sulfate and magnesium sulfate.

8. The method, according to claim 1, wherein the spores are grown to a concentration in excess of $1.0 \times 10^7$ spores/ml when the concentration of spores is measured by withdrawing a 20 μL sample from a region of the culture with the highest concentration of sporulated *Pasteuria*, based on microscopic observation, diluting the sample to 1 mL with sterile deionized water, subjecting the sample to sonication for one minute at 15 watts on a Fisher Sonic Dismembrator Model 60, and then measuring the spore density with a hemacytometer.

9. The method, according to claim 1, wherein the oxidation reduction potential of the medium is maintained at about 50–150 mV and sporulation is induced by increasing the oxidation reduction potential to about 150–200 mV.

10. The method, according to claim 1, wherein said growth medium is free of nematode tissue.

11. The method, according to claim 1, wherein said *Pasteuria* are grown in vitro for at least 24 days.

12. The method, according to claim 1, wherein said *Pasteuria* are grown in vitro for at least 46 days.

* * * * *

UNITED STATES PATENT AND TRADEMARK OFFICE
CERTIFICATE OF CORRECTION

| | | |
|---|---|---|
| PATENT NO. | : 7,067,299 B2 | Page 1 of 1 |
| APPLICATION NO. | : 10/460581 | |
| DATED | : June 27, 2006 | |
| INVENTOR(S) | : John F. Gerber et al. | |

It is certified that error appears in the above-identified patent and that said Letters Patent is hereby corrected as shown below:

Column 17,
Line 26, Table 9, Row 4, "In Vivo" Column, "0" should read --20--.

Signed and Sealed this

Seventh Day of November, 2006

JON W. DUDAS
*Director of the United States Patent and Trademark Office*